United States Patent [19]

Cassou

[11] Patent Number: 4,522,621

[45] Date of Patent: Jun. 11, 1985

[54] ARTIFICIAL INSEMINATION APPARATUS

[75] Inventor: Bertrand Cassou, Saint Symphorien des Bruyeres, 61300 l'Aigle, France

[73] Assignees: Bertrand Cassou; Robert Cassou; Maurice Cassou, all of l'Aigle, France

[21] Appl. No.: 457,923

[22] Filed: Jan. 14, 1983

[30] Foreign Application Priority Data

Jan. 26, 1982 [FR] France ................................ 82 01173

[51] Int. Cl.$^3$ ........................ A61M 37/02; A61D 7/02

[52] U.S. Cl. .................................... 604/140; 604/146; 604/181

[58] Field of Search ........................ 604/37, 38, 49, 54, 604/55, 59-61, 132, 135, 140, 146, 181, 186, 217; 128/1 R

[56] References Cited

U.S. PATENT DOCUMENTS

| | | | |
|---|---|---|---|
| 2,942,603 | 6/1960 | Geyer . | |
| 3,343,539 | 9/1967 | Moorhouse . | |
| 3,880,210 | 4/1975 | Randolph et al. | 128/1 R |
| 4,082,121 | 4/1978 | Sturm et al. | 604/125 |
| 4,432,753 | 2/1984 | Cassou | 604/55 |

FOREIGN PATENT DOCUMENTS

| | | | |
|---|---|---|---|
| 1394416 | 2/1965 | France | 604/55 |

*Primary Examiner*—C. Fred Rosenbaum
*Assistant Examiner*—Michelle Lester
*Attorney, Agent, or Firm*—Kenyon & Kenyon

[57] ABSTRACT

The invention relates to "insemination guns" comprising an elongate body (1) at the front end of which is fixed an insemination tube (10) ("paillette") and within which is slidingly mounted an ejection rod for ejecting the tube, while an air supply is connected by an air flow passage to the tube (10) at the front end (5*a*) of the body.

The problem posed is to provide such an apparatus which is easy to manipulate and simple to maintain.

According to the present invention, the ejection rod (6) has at least one flat (16) cooperating with the circular section wall of the conduit (5) in which the ejection rod is mounted to define the air flow passage (17) beside the ejection rod (6) in the conduit.

The invention is especially applicable to inseminating turkeys.

17 Claims, 5 Drawing Figures

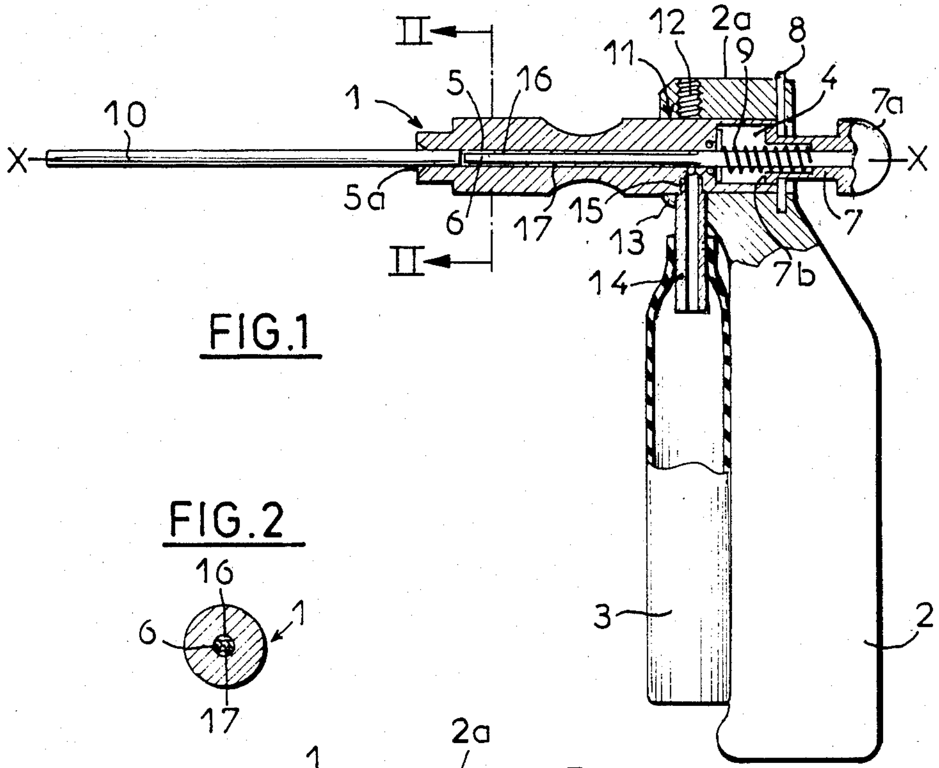
FIG.1
FIG.2
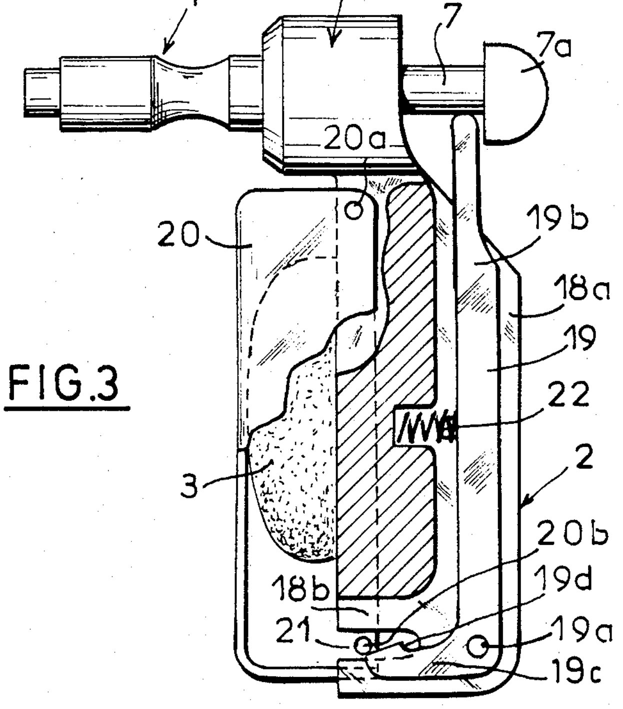
FIG.3

ARTIFICIAL INSEMINATION APPARATUS

BACKGROUND OF THE INVENTION

The present invention relates to apparatus, called "guns" for single-shot artificial insemination of animals such as poultry, and more especially turkeys, of the kind comprising on one hand an elongate body presenting an axial conduit into the front end of which the end of an insemination tube can penetrate and be maintained, and in which is mounted slidingly a rod for ejecting the tube, solid with an external manually actuable member, and on the other hand a compressible envelope connected by a flow passage to said front end of the axial conduit in the body.

The insemination tube, called a "paillette" (or "French straw") is designed to receive a dose of animal semen, either by means of a special filling machine, in which case the tube is filled before it is fitted onto the gun, or using additional suction means provided on the gun itself, in which case the tube is filled by suction after it is fitted on the gun. In each case, once the gun is fitted with its tube filled with the desired dose of semen, the inseminator introduces the tube into the cloaca of the animal by pushing it by means of the gun into the desired optimum position, after which he compresses the envelope, which is filled with air so that the air flows through the passage provided, and urges the semen out under sufficient pressure for the semen to reach the position of the utero-vaginal glands, thus ensuring insemination in the best conditions.

DESCRIPTION OF PRIOR ART

It is already known, for example from French Pat. No. 81 04551 to provide guns of the type referred to in which the ejection rod is hollow and the compressible envelope fits onto its end opposite to the insemination tube, being accommodated in an elongate axial chamber in the body, so as to follow the motion of the rod during the ejection movement, while the manually actuable member of the rod, fixed on the side of the rod, projects transversely out of the body. The same manually actuable member also incorporates the additional suction means provided in the second design referred to above. It is important to note that the three operations of penetrating into the cloaca, the actual insemination operation, and ejection of the paillette can be performed by the inseminator using one hand holding the body of the gun, the manually actuable member being actuated by the thumb of the same hand while the other hand is free to grasp the animal and hold it during the insemination.

It happens, however, that since the shape of the gun is basically cylindrical and directed along the axis of the paillette, the manipulation is not always easy, at least for certain of the inseminators, all the more so since the actual insemination operation by squashing the compressible envelope requires a hand position which is right towards the back of the gun. Moreover, the mechanism is relatively complex, due in part to the presence of the special suction members, leading to increased risk of fouling up, and particular difficulties in maintenance.

Furthermore, it is not very easy given that the ejection rod is tubular, to ensure that its central channel coincides with a source of air, particularly if the flow of air arrives in a radial direction, that is to say perpendicular to the ejection rod. Given that the ejection rod is mounted slidingly, it is necessary in this case to ensure the communication between the source of air and the rod by relatively complex circuits, which constitutes a serious disadvantage.

OBJECT OF THE INVENTION

The object of the present invention is therefore to provide apparatus of the kind referred to whose manipulation is easy and whose manufacture and maintenance are simplified.

SUMMARY OF THE INVENTION

The present invention provides artificial insemination apparatus comprising a body defining a conduit having a front end for receiving an end of a tube containing a dose of semen, an ejection rod mounted slidingly in said conduit and manually displaceable from a rear portion thereof remote from said front end of said conduit, and air supply means communicating with said conduit for supplying air under pressure to expel the semen from said tube, said conduit being generally circular in section and said ejection rod being formed with a non-circular section, whereby to define at least one air flow passage extending in said conduit beside said ejection rod from said front end of said conduit to said communication with said air supply means whereby to duct air from said air supply means to said tube.

In a preferred embodiment of the invention said body comprises a hand-grip portion extending generally transversely to said conduit, said air supply means comprising a compressible envelope disposed on said grip portion at a front side thereof.

Due to this arrangement, the inseminator can readily and firmly grasp the gun by the grip part, and fit the front end of the axial conduit of the body onto the end of the tube or paillette by a simple thrust movement, the paillette being generally presented by a distributor or even by a filling machine, such as that described in French Pat. No. 81 03253, for example. Once the paillette is well inserted into the conduit, the inseminator introduces it into the animal's cloaca by pushing the gun using the grip, the grip also serving to direct the paillette and to make it follow the sinuous utero-vaginal conduit, after which firm pressure of the fingers on the compressible envelope placed in front of the grip enables energetic ejection of the semen. The inseminator must not then relax the pressure on the envelope, so as not to risk sucking back up the dose of semen which he has just deposited, until the paillette has been taken out of the cloaca. A simple movement of the thumb on the manually actuable member of the ejection rod, fixed on the body enables the paillette to be separated and a complete new cycle of operations to be performed.

Advantageously, it may be arranged that the air flow passage extends along the ejection rod between a communication passage extending transversely to said rod and said front end of said conduit. This arrangement avoids forming a passage axially within the ejection rod, which would be of small diameter and difficult to clean.

The air flow passage may be formed by a flat on the ejection rod, and preferably said ejection rod is of part-circular section, with two diametrically opposite flats extending along said rod whereby to define two said air flow passages.

In one embodiment of the invention, said body comprises a barrel portion fitted in said grip portion, and means for securing said barrel portion and said grip portion together. Preferably said grip portion comprises a part projecting towards said front end for receiving said barrel portion, said projecting part presenting a duct extending transversely to said conduit and providing said communication between said envelope and said conduit.

Advantageously, said duct is formed in a tube member engaging in an opening formed in said projecting part.

These complementary features enable the different components to be assembled together fitting into simple circular cylindrical openings which are simple to clean, and disassembly is also easy to arrange, for example if the means securing the barrel portion and grip portion together comprises a screw, and if the envelope fits onto the tube member providing the communication duct, the tube member fitting into the grip.

In a particularly advantageous manner, it may be arranged that said ejection rod comprises a manually actuable member extending rearwardly out of said body for displacing said ejection rod. This facilitates ejection of the insemination tube by a simple movement of the thumb at the rear of the gun.

DESCRIPTION OF THE DRAWINGS

Other features and advantages of the invention will appear from the following description, given by way of example with reference to the accompanying drawings, in which:

FIG. 1 is a side view, partly in section, of an insemination gun in accordance with a first embodiment of the invention.

FIG. 2 is a sectional view of the body of the gun taken on the line II—II of FIG. 1.

FIG. 3 is a view similar to FIG. 1 of a second embodiment of the invention.

DESCRIPTION OF THE EMBODIMENTS

Figure 4:
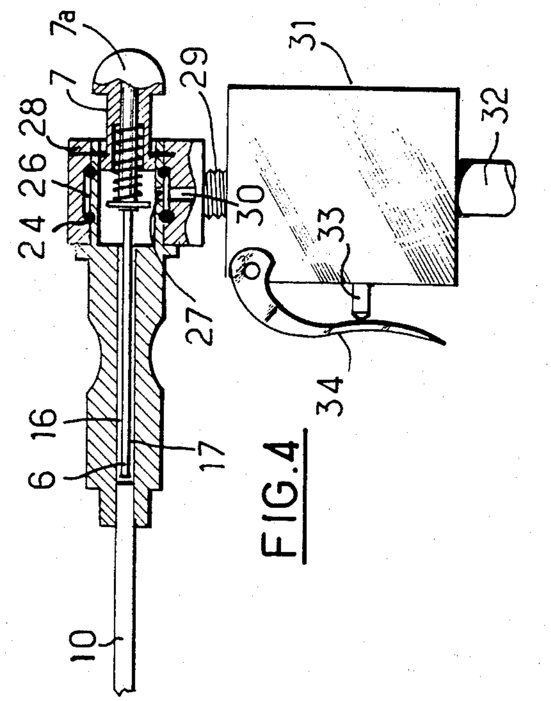
FIG. 4 is a view, partly in section, of a gun according to an alternative design.

The gun illustrated comprises on one hand, a cylindrical body 1 forming a barrel, and on the other hand a transverse butt 2 on the front of which is disposed an air envelope 3.

The body or barrel 1 comprises a solid part in the rear of which is formed a cylindrical chamber 4 and through which passes a guide conduit 5 extending through the whole of the rest of the length of the barrel in its axis X—X. Inside the conduit 5, an ejection rod 6 is mounted slidingly and extends through the whole length of the conduit, apart from a relatively short front part 5*a*, and through the whole chamber 4 so as to project out of the chamber where it bears, fixed on the rod, a cylindrical sleeve 7 having a semi-spherical rounded head 7*a* forming a push-button. At its inner end, the sleeve 7 also presents a collar 7*b* which is mounted slidingly in the chamber 4, and behind which engage two arms of a stirrup-shaped member 8 which pass through parallel transverse conduits formed in the butt 2. A return spring 9 is disposed between the bottom of the chamber 4 and the sleeve 7, so as to urge the sleeve backwards towards a position engaging the stirrup 8.

The part 5*a* of the conduit 5, left free at the front of the rod 6 when it is maintained in its return position by the spring 9 acting on the push-button 7 accommodates the introduction of the end of a paillette or reservoir tube 10 of diameter corresponding to that of the conduit, so as to enable a tight fit.

The grip member 2 in the form of a butt presents an actual grip part shaped to fit in the hand, and which is extended upwards by an upper part 2*a* through which passes a cylindrical aperture 11 in which the cylindrical rear part of the body 1 engages, this part of the body being secured in place by means of a locking screw 12 which extends radially through the upper part 2*a* of the butt. The rear face of the body 1 stops short of the rear face 2*b* of the upper part 2*a* of the butt, so that the stirrup 8 can pass behind the body to maintain the collar 7*b* of the sleeve 7. The base of the stirrup 8 also rests on the upper face of this part 2*a* of the butt.

The same upper part 2*a* of the butt projects forwards relative to the main part 2 and a conduit 13 is formed downwards in this projecting part so as to receive a tube 14 which projects downwards out of this conduit so as to penetrate into an orifice 3*a* which the envelope 3 presents. The envelope is in the form of an elongate bulb formed compressibly of elastic material such as rubber. Its lateral surface rests against the front face of the main part 2 of the butt, extending over most of the height of the part 2.

The conduit 13 is formed in the upper part 2*a* of the butt, slightly in front of the chamber 4 of the body 1, so that the end of the tube 14 can also penetrate into a connecting passage 15 formed radially in the body 1 and opening into the axial conduit 5 of the body. Starting from the position of this conduit 15, two flow passages are formed between the conduit 5 and the rod 6 as far as the front end of the rod, these passages being defined by two parallel flats formed in the thickness of the rod 6 on diametrically opposite sides thereof. The passages 17 thus defined give communication of the passage 15, and hence the tube 14 and envelope 3 with the front end 5*a* of the conduit 5, and thus with the inside of the paillette 10 fixed therein. A seal is provided round the rod 6 behind the conduit 15 to avoid air from the envelope 3 escaping towards the chamber 4.

The operation of the gun described above is as follows:

in the normal position of use, the envelope 3 is normally filled with air and it is in communication with the exterior by the tube 14 and the conduit 5. The inseminator then grasps firmly the butt 2 of the gun, and applies the front end of the barrel 1 to the distributor or the machine which carries the semen paillettes 10, so that one of the paillettes is fitted into the end 5*a* of the conduit under the effect of the pressure of the palm of the hand on the butt 2 alone.

the inseminator then takes the gun away, and with it the paillette fitted into it, and puts the paillette into the cloaca of the animal to be inseminated, again using in this movement the pressure of his palm on the butt 2, the butt also aiding small movements in the lateral direction.

the inseminator then presses firmly on the envelope or bulb 3 and the large quantity of air which is thus ejected into the tube 14 and sent forward by the flow passages 17 pushes the dose of semen contained in the paillette 10 out to the optimum place within the utero-vaginal tract of the animal.

the inseminator avoids relaxing the pressure on the envelope 3, and brings the gun and paillette out, after which a simple movement of the thumb on the push-button 7*a* causes the rod 6 to eject the paillette 10 out of the body 1 of the gun.

The gun shown in FIG. 3 has a large part of its mechanism identical to that of the previous embodiment, and for this reason the whole of the upper part of this gun is shown in external view.

However, as shown in FIG. 3, the main part of the butt presents a relatively deep slot, extending both rearwardly at 18*a* and to the bottom end at 18*b*. Within this double slot, is disposed a lever with two arms 19 which is pivotted at 19*a* between the two lateral cheeks that define the slots 18*a* and 18*b*, the longer one of the arms 19 extending through the slot 18*a* so that its end is positioned behind the collar-push-button 7*a* of the sleeve 7, while the other, shorter, arm 19*c* is disposed in the lower slot 18.

A member similar to the trigger of a piston is also provided, comprising a stirrup which extends over the whole height of the butt 2 and whose arms embrace the compressible envelope 3 which is filled with air. The stirrup 20 is pivotted transversely on the butt 2 at 20*a* at its upper end, and its lower end is provided with a transverse pin 20*b* which extends through two slots 21 formed in the lower cheeks of the butt in an arc of a circle centred on the pivot 20*a*. In the normal position, that is to say with the envelope 3 filled normally and not squashed, the stirrup 20 extends almost vertically on the butt, and the transverse pin 20*b* stays positioned at the front of the slots 21 in front of a tooth 19*d* which is formed at the end of the lower arm 19*c* of the lever and extends upwards. Lastly, a return spring 22 is disposed between the bottom of the slot 18*a* and the elongate arm 19*b* of the lever.

The apparatus operates in a manner identical to the apparatus of FIGS. 1 and 2, apart from the following difference:

once the paillette is introduced into the animal's cloaca, the inseminator squashes the envelope 3 with his fingers by pressing on the trigger/stirrup 20 which thus tilts rearwards. In this movement, the transverse pin 20*b* moves back in the slots 21 and locks in behind the tooth 19*d* on the arm 19 which moves away temporarily by compressing the spring 22. Thus, the stirrup is maintained in the rearward position by the engagement of the tooth 19*d*, and this keeps the envelope 3 compressed so that the inseminator can take the gun out without having to take special care to keep his fingers squashing the butt. In this way all risk of the ejected dose outside the paillette being sucked back up again is avoided.

once the gun is removed, when the thumb is applied to the push-button 7*a* to eject the paillette 10, the button also engages the end of the elongate arm 19*b* of the lever and tilts the lever, thus freeing the pin 20*b* and the stirrup 20 which return to the normal position. The envelope 3 fills up with air again ready for the next operation.

In the variant shown in FIG. 4, the artificial insemination apparatus or gun comprises a barrel 1 which is similar to that shown in FIG. 1, except that this barrel 1 has the feature that it comprises a collar 23 disposed adjacent its rear part, and two "O" ring seals 24, 25 which define between them an annular space 26 into which opens a radial orifice 27 extending transversely through the barrel.

On the rear part of the barrel, a connector 28 in the form of a sleeve is fitted sealingly, the connector being positioned on the two "O" ring seals 24, 25 which seal the connector. The connector comprises a threaded nozzle 29 through which passes an orifice 30, the orifice opening into the annular space 26 of the barrel and being directed to face the orifice 27. The threaded nozzle 29 is threadingly connected to a connector 31 which itself is coupled to a source of slightly compressed air. In known fashion, the connector 31 encloses a valve (not shown) controlled externally by a push-button 33 controlled by a trigger lever 34. Action of the hand on the trigger 34 presses the push-button 33 and liberates, as desired, a certain quantity of air which is ducted to the paillette or reservoir tube through the orifices 30 and 27 which in turn communicate with the passages 17 defined by the flats 16 formed along the ejector rod 6. The actual ejection part of the mechanism is similar to that shown in FIG. 1, as illustrated in FIG. 4.

Figure 5:
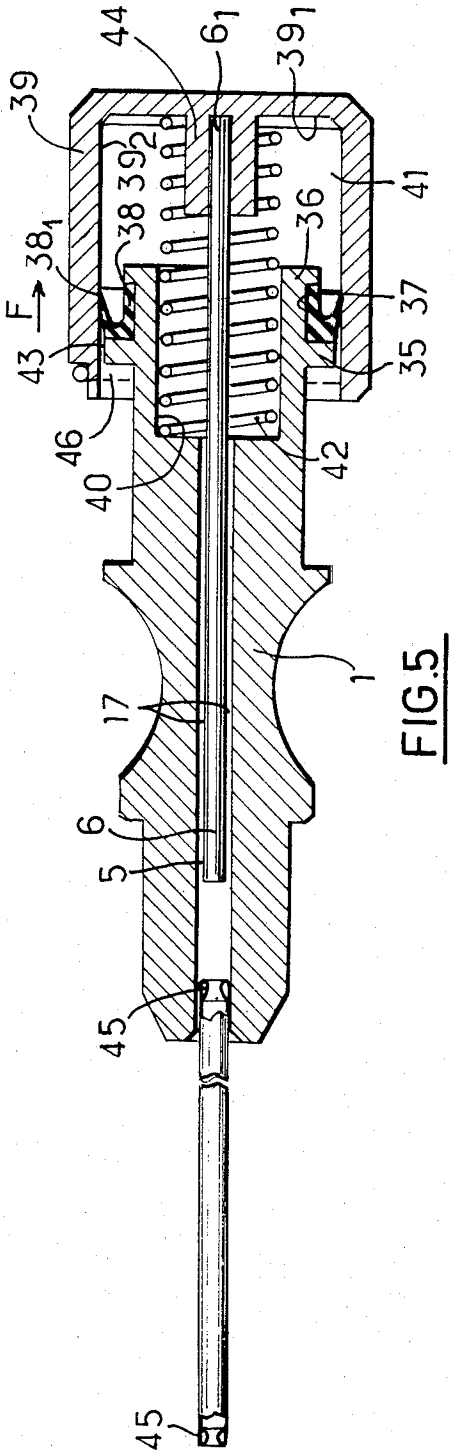
FIG. 5 is an axial sectional view of yet another embodiment of the invention.

In another embodiment, as shown in FIG. 5, the gun is of the linear kind and operates in the same way as a bicycle pump. In this case, the barrel 1 bears on its rear part a double annular collar 35, 36 defining between them an annular recess 37 in which is fitted a lip-seal 38 sealing the body of the barrel to a shell 39 in the form of a cap mounted axial alternating translation motion relative to the barrel, the shell defining, with a recess 40 formed in the rear face of the barrel, a chamber 41 accumulating air. The shell 39 is urged permanently rearwards, that is to say in the direction away from the paillette, by a coil spring 42 which engages in the bottom of the recess 40 and against the internal front face $39_1$ of the shell 39.

The seal 38 comprises a flexible lip $38_1$ which is inclined slightly outwards the internal peripheral wall $39_2$ of the shell 39, the lip extending in the same direction as the thrust of the spring 42 (arrow F) so that during the translatory displacement of the shell 39 towards the paillette 10, the lip $38_1$ of the seal 38 is applied sealingly against the internal wall $39_2$, whereas when the shell returns to its initial position by sliding in the opposite direction (arrow F) the lip $38_1$ disengages radially inwards to enable external air to pass and be introduced into the chamber 41 through an annular gap 43 formed between the collar 35 of the barrel and the internal wall $39_2$ of the shell. In other words, the return of the shell 39 in the direction of the arrow F enables the gun to be loaded by introduction and accumulation of air in the chamber 41, whereas the displacement of the same shell in the opposite direction ensures the transfer of the air contained in the chamber 41 into the paillette 10 by passing through the axial passages 17 defined by the flats 16 formed on the ejector rod 6. The ejector rod 6 is fixed by its rear part $6_1$ into an internal boss 44 on the shell and is guided over its whole length in the conduit 5 of the barrel.

As shown in FIG. 5, the paillette 10 may comprise a rim 45 at at least one of its ends and, if necessary, this rim may be repeated at the opposite end.

As in the other embodiments, a stirrup 46 secures the barrel to the shell 39, the stirrup having two branches engaging the annular collar 35 of the barrel to prevent the shell 39 coming off. The translatory stroke of the shell 39 corresponds to the stroke of the ejector rod which is solid with it, and whose stroke is limited by abutment of the front face of the rod with the rear end of the insemination tube. The contact between the rod and the tube is sufficient to be felt by the operator's hand, and when he feels this resistance, appreciates that the insemination operation is completed, and he can then extract the tube from the animal's cloaca and finishing pressing the shell towards the tube so that the ejector tube 6 ejects it from the nose of the body 1.

I claim:

1. Artificial insemination apparatus comprising a body defining a conduit having a front end adapted to receive an end of a tube containing a dose of semen, an ejection rod mounted slidingly in said conduit and manually displaceable from a rear portion thereof remote from said front end of said conduit, and air supply means communicating with said conduit for supplying air under pressure to expel the semen from said tube, said conduit being generally circular in cross-section; and said ejection rod being formed with a non-circulator cross-section; thereby defining at least one air flow passage extending longitudinally in said conduit adjacent said ejection rod from said front end of said conduit to said communication with said air supply means so as to conduct air from said air supply means to said tube.

2. Apparatus as claimed in claim 1, wherein said ejection rod is of part-circular section, with two diametrically opposite flat surfaces extending along said rod thereby defining two said air flow passages.

3. Apparatus as claimed in claim 1 or 2 wherein said body further comprises a hand-grip portion extending generally transversely to said conduit, said air supply means comprising a compressible envelope disposed on said grip portion at a front side thereof.

4. Apparatus as claimed in claim 3 wherein said body further comprises a barrel portion fitted in said grip portion, to means for securing said barrel portion and said grip portion.

5. Apparatus as claimed in claim 3 wherein said grip portion includes a portion projecting towards said front end for receiving said barrel portion, said projecting portion including at least a portion of a duct which extends transversely to said conduit and provides said communication between said envelope and said conduit.

6. Apparatus as claimed in claim 5 wherein said duct is formed in a tube member engaging in an opening formed in said projecting portion.

7. Apparatus as claimed in claim 6 wherein said duct further comprises a passage formed in said barrel portion.

8. Apparatus as claimed in claim 1 wherein said ejection rod is coupled to a manually actuable member extending rearwardly out of said body for displacing said ejection rod.

9. Apparatus as claimed in claim 4 wherein said ejection rod is coupled to a manually actuable member extending rearwardly out of said body and including an abutment which is disposed slidingly in a chamber formed in said body, and said body includes a stop member extending in said chamber transversely of said rod and cooperating with said abutment so as to provide a rest position for said manually actuable member in which it is disposed forwardly of a rear side of said grip portion.

10. Apparatus as claimed in claim 3 wherein said air supply means further comprises a compression member displaceable between a compression position in which it compresses said envelope and a rest position in which it relaxes said envelope and locking means for locking said compression member in said compressed position said locking means being coupled with said ejection rod for releasing said compression member to said rest position when said ejection rod is actuated.

11. Apparatus as claimed in claim 10 wherein said compression member is pivoted on said grip portion and said locking means includes a lever having a first end portion coupled for displacement with said ejection rod and a second end portion bearing latch means for engaging said compression member to lock it and release it.

12. Apparatus as claimed in claim 1 wherein said air supply means comprises connection means for connection to a source of compressed air, and manually actuable valve means for releasing air from said connection means to said communication with said conduit.

13. Apparatus as claimed in claim 12 wherein said body includes first and second "O" ring seals which define therebetween an annular space, and an orifice extending radially to said ejection rod and into said annular space to provide communication with said conduit.

14. Apparatus as claimed in claim 1 wherein said air supply means comprises a rear portion of said body which defines a chamber, a manually displaceable cover member covering said chamber, lip seal means for sealing said cover member to said rear portion of said body during movement of said cover member to compress said chamber and for relaxing to admit air to said chamber during return movement of said cover member, and return spring means for urging said cover member towards the direction of said return movement.

15. Apparatus as claimed in claim 14 wherein said ejection rod is secured to said cover member to move therewith, the compression stroke of said cover member to supply air to expel semen from said tube being limited to a stroke which brings said ejection rod into engagement with said end of said tube.

16. Apparatus as claimed in claim 15 wherein said cover member is retained on said body by a transverse abutment on said cover member cooperating with an abutment projecting from said body member.

17. Apparatus as claimed in claim 1 wherein said tube containing semen includes a rim at at least one of its ends.

* * * * *

UNITED STATES PATENT AND TRADEMARK OFFICE

CERTIFICATE OF CORRECTION

PATENT NO. : 4,522,621

DATED : June 11, 1985

INVENTOR(S) : Bertrand Cassou

It is certified that error appears in the above-identified patent and that said Letters Patent is hereby corrected as shown below:

Col. 3, line 9, after "together" insert --,--.
Col. 3, line 11, after "example" insert --,--.
Col. 3, line 13, change "comprises" to --comprise--.
Col. 3, line 26, after "example" insert --,--.
Col. 3, line 42, after "hand" insert --,--.
Col. 3, line 65, after "7" insert --,--.
Col. 4, line 34, after "3" insert --,--.
Col. 5, line 7, change "pivotted" to --pivoted--.
Col. 5, line 13, change "piston" to --pistol--.
Col. 5, line 17, change "pivotted" to --pivoted--.
Col. 5, line 21, change "centred" to --centered--.
Col. 6, line 18, after "mounted" insert --for--.
Col. 6, line 22, after "say" insert --,--.
Col. 6, line 27, after "outwards" insert --of--.
Col. 6, line 34, after "(arrow F)" insert --,--.
Col. 6, line 34, delete "," after "lip 38".
Col. 6, lines 63 and 64, change "finishing" to --finish--.

In the Claims:

Col. 7, line 7, delete ";".
Col. 7, line 9, after "cross-section" change ";" to --,--.

UNITED STATES PATENT AND TRADEMARK OFFICE

CERTIFICATE OF CORRECTION

PATENT NO. : 4,522,621

DATED : June 11, 1985

INVENTOR(S) : Bertrand Cassou

It is certified that error appears in the above-identified patent and that said Letters Patent is hereby corrected as shown below:

Col. 7, line 26, before "means" delete "to" and insert --and--.
Col. 7, line 26, after "portion" delete "and" and insert --to--.
Col. 8, line 8, after "position" insert --,--.
Col. 8, line 9, after "being" insert --operatively--.

Signed and Sealed this

*Seventh* Day of *January 1986*

[SEAL]

*Attest:*

DONALD J. QUIGG

*Attesting Officer*

*Commissioner of Patents and Trademarks*